United States Patent [19]

Schinkmann et al.

[11] 4,401,547
[45] Aug. 30, 1983

[54] POLAROGRAPHIC APPARATUS WITH DETACHABLE SAMPLE CHAMBER FOR MEASURING BLOOD GASES

[75] Inventors: Manfred Schinkmann; Hans-Jürgen Busack, both of Lübeck, Fed. Rep. of Germany

[73] Assignee: Drägerwerk Aktiengesellschaft, Fed. Rep. of Germany

[21] Appl. No.: 188,722

[22] Filed: Sep. 23, 1980

[30] Foreign Application Priority Data

Sep. 22, 1979 [DE] Fed. Rep. of Germany ....... 2938433

[51] Int. Cl.³ .................... G01N 27/48; G01N 33/50
[52] U.S. Cl. .................... 204/415; 422/68; 436/68
[58] Field of Search .................... 422/68; 23/928; 204/195 P; 436/68

[56] References Cited

U.S. PATENT DOCUMENTS 4,157,288  6/1979  Fleckenstein .................. 204/195 P
4,265,250  5/1981  Parker ........................ 204/195 P X
4,269,685  5/1981  Parker ........................ 204/195 P

*Primary Examiner*—Sidney Marantz
*Attorney, Agent, or Firm*—McGlew and Tuttle

[57] ABSTRACT

A test apparatus for measuring blood characteristics comprises a measuring head having a measuring electrode and a reference electrode arranged in spaced relationship and a closure membrane covering a portion of said head, and an attachment connectable to said head having a wall defining a support membrane which is engageable on the closure membrane. The attachment defines a chamber for the blood sample in which the support membrane forms a bottom wall thereof so that the membrane supporting the blood is in contact with the closure member and thus is capable of being heated by a heater contained in the head without coming into contact with or contaminating the blood sample. The attachment while permitting the measurement to be made does not allow the blood being tested to come into contact with the measuring head. The attachment may be either disposed of or cleaned for re-use.

6 Claims, 1 Drawing Figure

U.S. Patent
Aug. 30, 1983
4,401,547
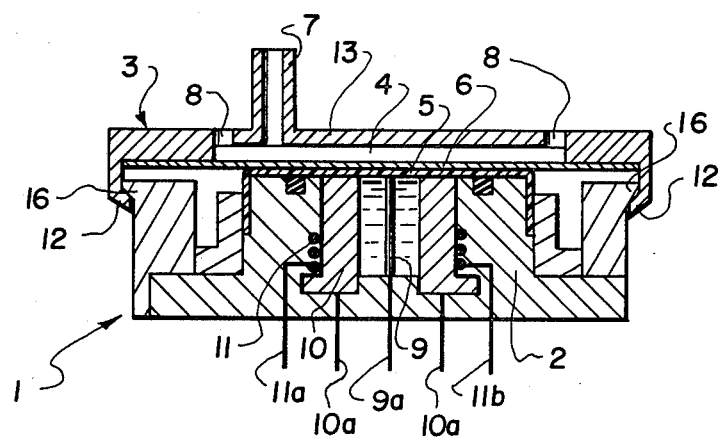

POLAROGRAPHIC APPARATUS WITH DETACHABLE SAMPLE CHAMBER FOR MEASURING BLOOD GASES

FIELD AND BACKGROUND OF THE INVENTION

This invention relates in general to testing apparatus and in particular to a new and useful device for testing blood samples which includes an attachment for connection to a measuring head and which comprises a chamber for the blood sample with a wall thereof which forms a membrane which engages over a closure membrane of the head.

The blood gas concentration is measured transcutane with known polarographic measurement heads placed on the skin of the patient. Reliable blood gas values can be obtained using transcutane measurements, where there is normal blood perfusion. However, in persons under shock, the perfusion is limited. In these cases the blood is to be measured directly. When applying the polarographic method only small blood amounts are sufficient from which the blood gas content can be determined.

Known measuring heads for measuring the blood gas content of small amounts of blood, for example two drops of blood, employ heated polarographic measuring heads, which up to now have been usable for the transcutane measurement of the perfusion efficiency. For this purpose they are screwed from below into the concentric opening of a body made, for example, from plexiglass. In this case the membrane surrounding the electrolyte fits to a well heat-conducting ring in a plexiglass body. This ring is provided with a conical bore forming a funnel shaped measuring trough. This trough is provided in its lower part with a bore which can be connected via an outlet with a suction pump. This bore can be closed with a cock. The blood amount entered into the trough stands on the membrane of the measuring head closing the trough opening at the bottom. The blood maintains the properties as in the core region of the blood vessels by the heat fed from the measuring head into the ring. The blood gas passes through the membrane of the measuring head into the electrolyte and is then determined. It is a disadvantage of this test system that the blood touches the membrane of the measuring head and that the head as well as the plexiglas body, has to be cleaned after each measurement. The sensitive membrane is easily damaged thereby, but at least it is worn off. Successive exchange and new calibration of the measuring head require considerable assembly work. (DE-OS No. 23 47 779).

SUMMARY OF THE INVENTION

The invention provides an apparatus for the discrete determination of the blood gas concentration in a blood amount of from 2 to 200 $\mu$l, which can be handled safely and easily.

In accordance with the invention the measuring head is provided with a closure member or membrane which covers a portion thereof and an attachment is fittable to the head and it includes a blood sample chamber having a membrane wall which contacts the closure membrane so that the blood may be positioned directly on the head. The construction is such that the head, which contains a measuring electrode, and a reference electrode and a heater may be located directly below the blood sample in a position such that the closure cover or membrane of the head may heat up and contact a support membrane of the attachment so that blood carried thereby may also be heated.

The invention permits the combination of a known polarographic measuring head with an attachment having a receiving area for the blood and the blood to be tested does not come into contact with the measuring head and cannot soil it. Thus the prior art construction wherein the sensitive membrane must be removed and cleaned and thus exposed to possible damage or wear, is excluded. The temperature of the measuring head remains undisturbed between individual measurements. The assurance of the accuracy in the following measurements is not placed in danger. Successive measurements are particularly simple by employing attachments which are of the throw away type.

Accordingly it is an object of the invention to provide a test apparatus for measuring blood which comprises a measuring head which has a measuring electrode and a reference electrode arranged in spaced relationship and which includes a closure member covering a portion of the head, and further including an attachment which is connectable to the head and has an interior blood sample container chamber with a wall portion which is engageable over the closure member of the head.

A further object of the invention is to provide a test apparatus which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the Drawings:

The only FIGURE of the drawing is a sectional view of a measuring head with a removable attachment member thereon constructed in accordance with the invention.

DETAILED DESCRIPTION OF PREFERRED EMBODIMENT

Referring to the drawing in particular, the invention embodied therein comprises a test apparatus generally designated 1 for measuring blood characteristics which comprises a measuring head part 1 having a measuring electrode 9 with a connecting terminal 9a which extends out of the head and a reference electrode 10 having terminals or leads 10a, 10a. The reference electrode 10 is surrounded by an electric heater 11 having terminals 11a, 11b. A portion of the head 1 is covered by a member forming a closure membrane 5.

In accordance with the invention an attachment generally designated 3 is provided with end elements 12 permitting it to be snapped over shoulders 16 of the head 1. The attachment 3 includes a hollow space or chamber 4 for a blood sample which is admitted to the space 4 through an inlet connection 7. In accordance with a feature of the invention the chamber 4 is bounded by a support wall or blood contacting membrane or wall 6 which actually closes the bottom of the space 4. When the attachment is positioned correctly the membrane 5 will be in abutting contact with the membrane 6 so that the blood sample in the space 4 will be positioned for analysis as well as for heating by the heater 11.

The test apparatus generally designated 1 comprises the measuring head 2 connected to the attachment 3. It is important for the solution of the problem that the measuring head 2 does not contact the blood sample. The attachment 3 comprises the hollow space 4 for receiving the blood sample. This hollow space is toward the bottom, where it fits over the membrane 5 of the measuring head 2. The space is closed by the closing membrane 6. The inlet connector 7 is connected to the hollow space 4. Vent openings 8 in an upper cover 13 of the hollow space 4 render the introduction of the blood sample easier. The dimensions of the hollow space 4 can be selected for example to provide a volume in the region of from 2 to 200 $\mu$l.

The measuring head 2 comprises, besides the membrane 5, the known building blocks such as the measuring electrode 9 and the reference electrode 10, which can be heated by heater 11. It is heated to a temperature which is optimal for the determination of the blood gas concentration. A typical temperature region is from 36° C. to 45° C. The loaded attachment 3 is kept in position on the measuring head 2 by snap device or fitting 12; thereby the membrane 5 of the measuring head 2 and the closing membrane 6 are disposed close together.

The heat of the measuring head 2 with a temperature of for example 37.5° C. soon warms up the closing membrane 6 and the walls surrounding the hollow space 4 to a temperature of 37.5° C. After the filling in of the blood sample through inlet 7 the gas partial pressure of the blood sample is set in the electrode region of the measuring head through the abutment of the double membranes 5 and 6. Thus the blood gas concentration is measurable over the electrode.

After termination of the measurement the attachment 3 is removed from the measuring head 2 and is then either thrown away or independently from the measuring head subjected to a cleaning process with the object of renewed use. The measuring head 2 can be used again immediately. It does not come into contact with the blood sample.

While a specific embodiment of the invention has been shown and described in detail to illustrate the application of the principles of the invention, it will be understood that the invention may be embodied otherwise without departing from such principles.

What is claimed is:

1. A test apparatus for measuring blood gases comprising a measuring head having a measuring electrode and a reference electrode arranged in said head, a first closure gas permeable membrane covering a portion of said head, and an attachment connectable to said head having a blood sample container space with a second gas permeable membrane surrounding said space being engaged over and in contact with said closure membrane.

2. A test apparatus according to claim 1, including heater means associated with said head in a position to heat said closure membrane, said second membrane of said blood sample container being in heat conducting contact with said closure membrane.

3. A test apparatus according to claim 2, including an inlet connector connected into said blood sample container, and a vent opening for said sample container.

4. A test apparatus according to claim 2, including snap coupling means defined between said attachment and said head for interengaging said attachment with said head.

5. A test apparatus according to claim 1, wherein said blood sample container comprises a long shallow depth container arranged over said second membrane and having a volume of between 2 to 200 $\mu$l.

6. A test apparatus according to claim 1, wherein said attachment comprises a single use element.

* * * * *